United States Patent [19]

Cibley

[11] Patent Number: 4,461,305
[45] Date of Patent: Jul. 24, 1984

[54] AUTOMATED BIOPSY DEVICE

[76] Inventor: Leonard J. Cibley, 683 Beacon St., Newton Centre, Mass. 02159

[21] Appl. No.: 299,559

[22] Filed: Sep. 4, 1981

[51] Int. Cl.³ .............................................. A61B 10/00
[52] U.S. Cl. .................................... 128/754; 128/305; 128/751; 30/113.1
[58] Field of Search ...................... 128/305, 305.1, 310, 128/749, 751, 753–755; 30/113.1, 113.2, 130

[56] References Cited

U.S. PATENT DOCUMENTS

| | | | |
|---|---|---|---|
| 1,162,901 | 12/1915 | Cantey | 30/130 |
| 2,493,979 | 1/1950 | Kudd | 30/113.2 |
| 3,074,162 | 1/1963 | Lentini | 30/130 X |
| 3,512,519 | 5/1970 | Hall | 128/310 X |
| 3,683,892 | 8/1972 | Harris | 128/754 |

Primary Examiner—Kyle L. Howell
Assistant Examiner—Christine A. Fukushima
Attorney, Agent, or Firm—Limbach, Limbach & Sutton

[57] ABSTRACT

Disclosed herein is an apparatus for automatically extracting a sample of tissue of a predetermined size and shape from a body, e.g. female uterine cervix. The apparatus is generally comprised of a generally cylindrically core-cutter with a rotatably mounted cutting blade faired within the circumference of the cutting end of the core cutter for severing the tissue sample upon rotation of the blade. A plunger, slidably mounted within the core-cutter, is used to both limit the depth which the core-cutter advances into the tissue body and thus in part limit the size of the sample to be severed, and to expel or eject the severed sample in response to a forward movement of the plunger. An outer sleeve, preferably having a pronged edge located adjacent the cutting edge of the core cutter for properly positioning the apparatus against the tissue surface, telescopically surrounds the core cutter.

6 Claims, 12 Drawing Figures

U.S. Patent  Jul. 24, 1984  Sheet 1 of 3  4,461,305
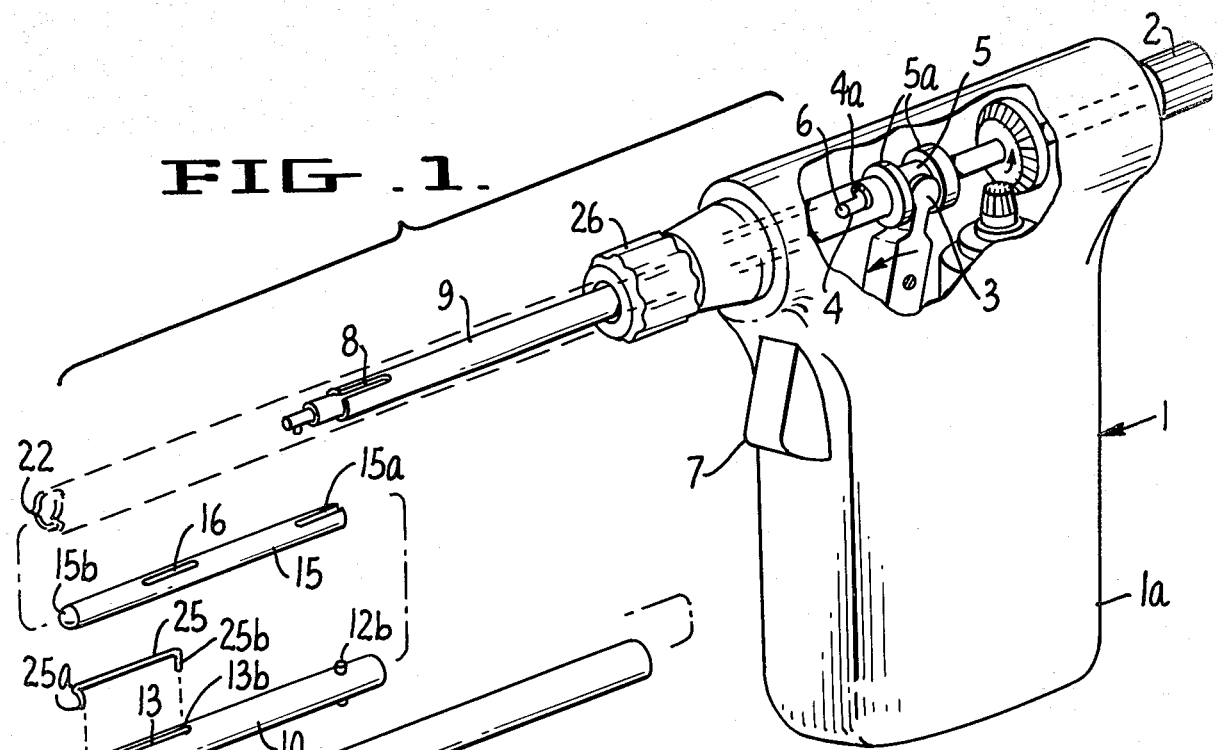
FIG. 1.
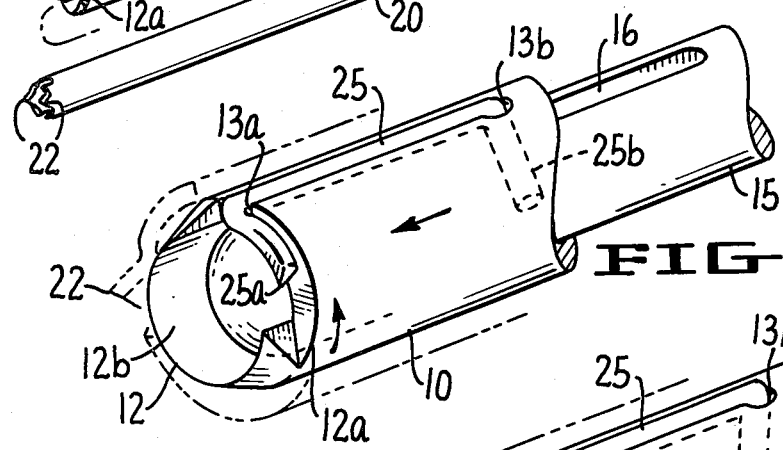
FIG. 2.
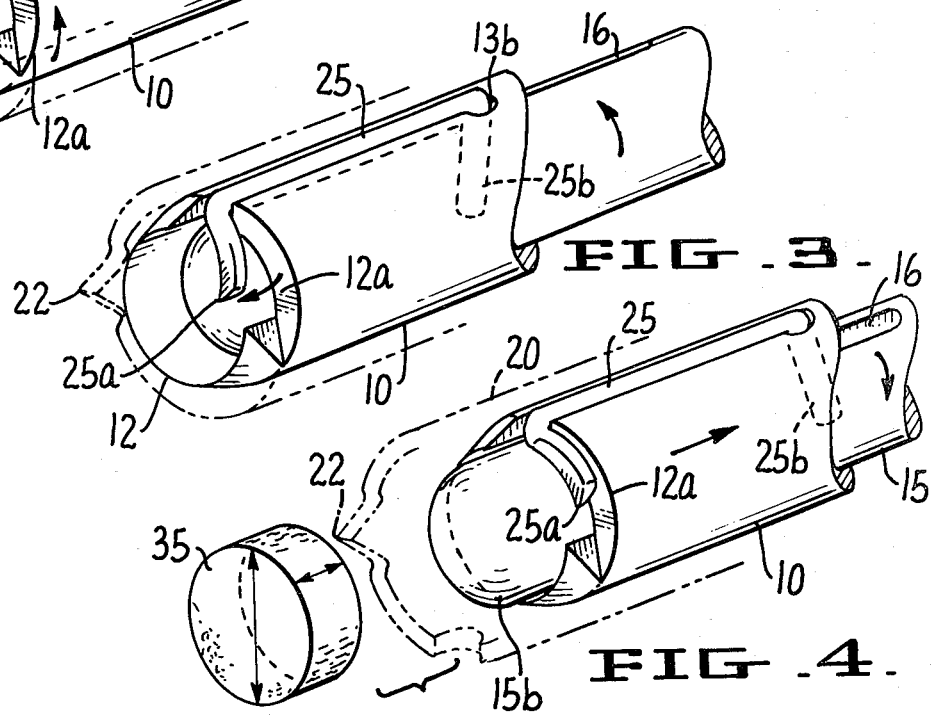
FIG. 3.
FIG. 4.

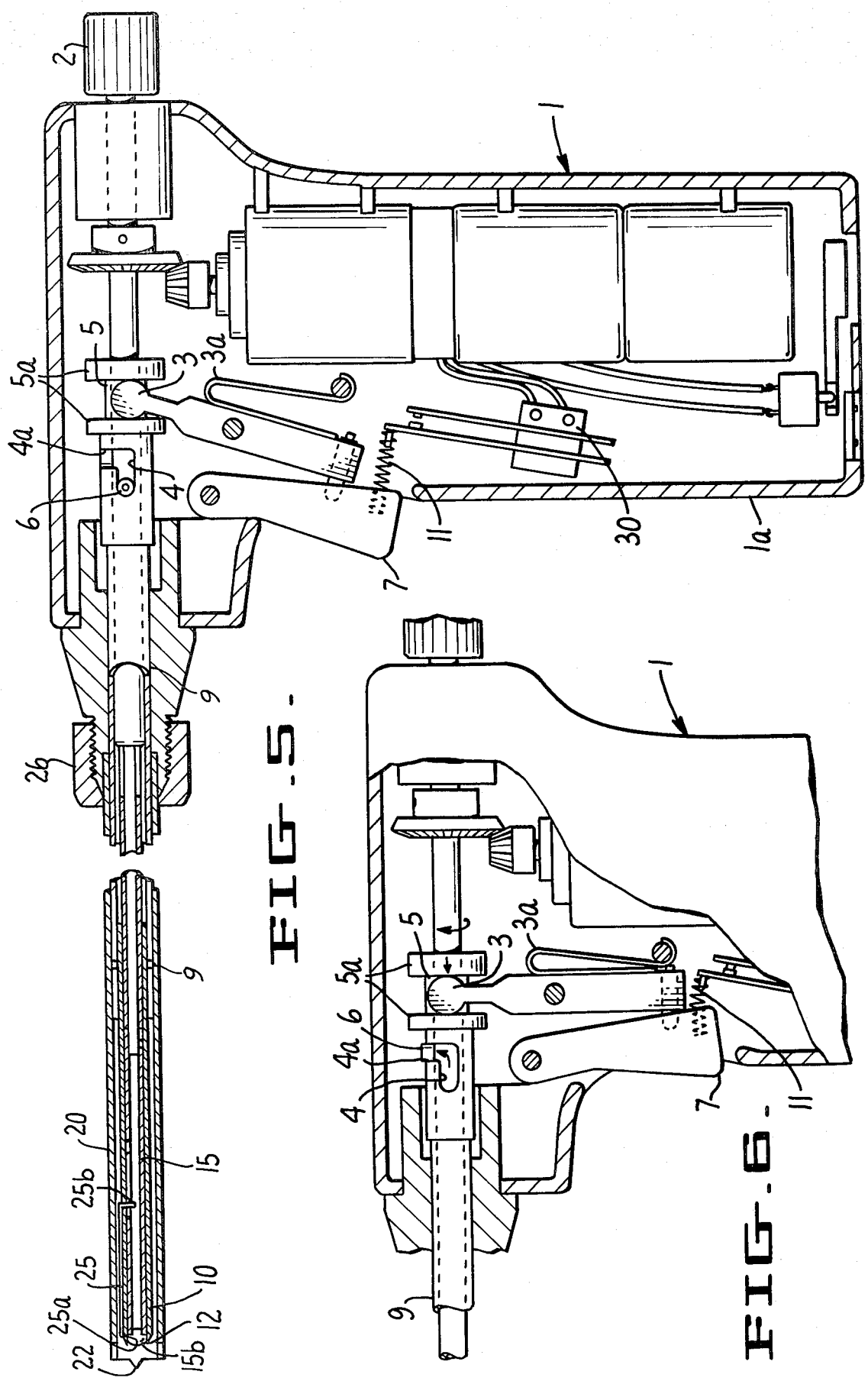

AUTOMATED BIOPSY DEVICE

FIELD OF THE INVENTION

The invention relates generally to the field of extracting tissue samples from solid bodies and more particularly the invention relates to the field of gynecology where one specific application of the invention is in extracting a biopsy or sample of tissue from the female uterine cervix and other areas.

BACKGROUND OF THE INVENTION

It is often desirable and necessary to sample or test a portion of a solid body, be it plant, animal or human, to determine certain characteristics and features of the whole body or a part of the larger body of tissue. Various means and apparatuses have been employed for the purpose of extracting a sample of tissue for testing and other purposes. Some of these apparatuses are the subject of certain specific patents of which applicant has knowledge. For example, U.S. Pat. No. 1,162,901 discloses an instrument for cutting cores from solid substances such as rosin from barrels. The instrument has a hollowed tube which has a rod with a cutting knife at one of its ends and a handle or means for rotating the knife to put its blade in a cutting position at the other end. The instrument is equipped with a spring biased plunger which is moved down the tube to force the piece of core out of the tube once it has been severed from the solid. The apparatus of the '901 patent must be heated to assist in the removal of the severed piece of core.

U.S. Pat. No. 3,683,892 discloses a device, comprised of a hollow extractor body, sharpened at one end, to receive a core of tissue cut by the sharpened end as the apparatus advances into the tissue body. The forward end of the sharpened extractor has a blade which is inwardly pivotal and which is responsive to the muscle tissue backflow to sever the base of the core of tissue from the surrounding tissue.

Still another means for severing a sample of tissue from a larger body has been disclosed in U.S. Pat. No. 2,493,979 in which a fruit-coring apparatus is claimed. Like the apparatus disclosed in the '901 patent, this fruit-coring apparatus also requires some pre-drilling into the body from which the sample is to be extracted, prior to the actual extraction of the sample. Thus, this apparatus, like the existing prior art apparatuses for extracting tissue samples, is rather time-consuming and may clearly result in great pain when being used to extract tissue samples from living animals, particularly humans.

The extraction of tissue samples from humans and other animals has been and is becoming even more prevalent in the diagnosis and treatment of patients for cancer, pre-malignant conditions, and/or other infections. Applicant has discovered at least one patent which is specifically directed to the application of obtaining a biopsy from human beings. This patent, U.S. Pat. No. 2,426,535, is directed to an infusion and a biopsy needle which is particularly applicable to the injection of fluid into a peripheral vein around tissue which has recently suffered extensive burns. The needle is likewise useful in extracting tissue from the same burned region.

U.S. Pat. No. 2,749,909 discloses a surgical instrument which may be used to extract a sampling of tissue from the female uterine cervix. The apparatus makes use of a conical, spiral cutting knife positioned such that the sampling of severed tissue is forced into the interior cavity of the apparatus where it is preserved until removed by the technician.

Perhaps the more growing need for having to extract samples of tissue from human beings is in the area of gynecology where a biopsy must be taken of a region of tissue for testing for cancerous or malignant cells.

Prior to taking a biopsy of tissue from the female uterine cervix, a PAP smear is usually performed. This PAP smear is done to test for the presence of abnormal cells arising from the uterus or cervix. The test is done on a sampling of cervix cells obtained by scraping a region of the cervix. The PAP smear exam may result in one of three findings: (1) benign, in which case no further test or biopsy is required; (2) precancerous, where there are cell changes which are called cervical intraepithelial neoplasia (CIN); and (3) malignant, or cancer.

In the case where there is a report of CIN from a PAP smear, a further test of a sample of the tissue from the uterine cervix is required. In obtaining this sample of tissue from the cervix, both the size and configuration of the sample is most important in arriving at an accurate examination of the sample for possible future treatment of the patient for cancer, pre-malignant conditions or other infections. In testing the sample of tissue for cancer, the actual size of the sample is of course important since the technician must have a large enough piece of tissue to make appropriate tests. But, even more important than the actual size of the sample of tissue is its configuration, since it is desirable from the technicians point of view to have a non-distorted sample of tissue so that the actual stage of development of the cancer or pre-malignant cells, or rather, how much the normal cell maturation process has been distorted and how far along the development of the immature cells has progressed, must be determined from the tissue sample being tested in order that future treatment of the detected disease may be as effective as possible.

There have been a number of prior art apparatuses for use in obtaining a biopsy of tissue from human beings from areas such as the female cervix. One such apparatus is a biopsy punch which is used primarily for extracting samples of tissue by surgical specialists and, in some cases, it is utilized in the area of dermatology for the same purpose. Despite this apparatus' possibly obvious application in the area of extracting samples from the cervix to test for cancer, it leaves much to be desired because the device, like the other prior art apparatuses, has minimal control over the actual size and shape of sample which is extracted. This biopsy punch, and other apparatuses which have been used for extracting tissue samples primarily from humans, and, more particularly from the female cervix, operates more or less on the principle of a pair of household scissors. That is, the apparatus, first of all, is manually operated, and, further, it depends on two pieces of the apparatus being pivoted about a lever or pivotal point to come together after being forced against the body of tissue to sever a sampling of the tissue body. With these types of apparatuses, it is, for the most part, impossible to control the actual size and, more importantly, the actual shape of the sample. The use of this and other biopsy punch apparatuses will inevitably result in irregularly shaped samples of tissue which may result in inaccurate test results. Quite clearly, it goes without saying that the need for as accurate a test result as possible in an area so vital to human beings as the test for cancer is of the utmost importance, for the result of such tests may clearly mean the difference between life and death.

STATEMENT OF THE INVENTION

Based on the foregoing discussion of the prior art apparatuses for biopsy samples from bodies, particularly human beings, and the actual present state of this art, it is apparent that there is a need in the art for an apparatus which is capable of automatically extracting a predetermined size and shape of a tissue sample from a body where this process can be done very quickly and results in minimal pain to the body from which the sample is extracted. It is further desirable that such an apparatus has a capability of extracting a sample of tissue which is of a predetermined size and of a non-distorted configuration. It is further desirable that the apparatus used to extract the sampling of tissue results in minimal physical harm to the body from which the sample is extracted.

Accordingly, I have invented an apparatus for automatically and quickly extracting a sampling of tissue from a body which makes use of a core-cutter with a cutting blade faired about the cutting edge of the core-cutter which, in one of its embodiments, further has a plunger mounted within the core-cutter for (1) controlling the depth that the core-cutter advances into the body of tissue, (2) prevent the movement of the sample of tissue within the core-cutter after the tissue has been severed from the body, and (3) ejecting the sample of tissue out of the core-cutter in response to a manual turn of a knob to return the core-cutter to its original position so that the tissue sample is expelled. The apparatus further has a means for rotating the cutting blade about the circumference of the core-cutter to sever a sample of tissue.

BRIEF DESCRIPTION OF THE DRAWINGS

The above noted advantages and other characteristic features of the present invention will be in part apparent from the accompanying drawings, and in part pointed out in the following detailed description of the preferred embodiment of the invention in which reference will be made to the accompanying drawings wherein like reference numerals designate corresponding parts and wherein:

FIG. 1 is an exploded perspective view of the inventive apparatus illustrating the major component parts of the apparatus with certain parts broken away;

FIGS. 2 through 4 are fragmentary perspective views showing the apparatus at different stages, with FIG. 2 illustrating the cutting blade in the non-cutting position, with FIG. 3 illustrating the cutting blade in the cutting position, and with FIG. 4 illustrating the cutting blade again in the non-cutting position after a sample of tissue has been severed, and with the tissue sample being expelled from the apparatus;

FIG. 5 is a side elevational view of the subject apparatus;

FIG. 6 is a fragmentary side elevational view shown in the alternate position;

DETAILED DESCRIPTION OF THE PREFERRED EMBODIMENTS

Figure 7:
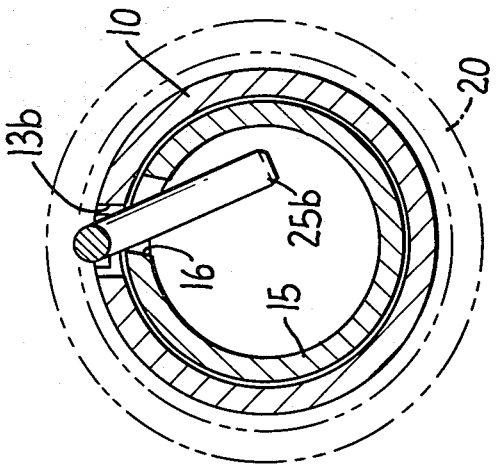
FIG. 7 is an enlarged end view of the cutting blade as it prepares to move in the cutting position.

Considering now the drawings in detail, FIG. 1 illustrates one embodiment of the inventive apparatus 1 with an exploded view of a number of its elements, including a cylindrical conduit 10 having a cutting edge 12 with a cut-away portion 12a, and with means 12b for operatively connecting said conduit 10 to drive means 5. Drive means 5 has an extended sleeve portion 9 which includes a slot 8 for receiving pin 12b of conduit 10. Conduit 10 further has an elongated slot 13 about its outer surface for receiving a cutting wire 25. Slot 13 of conduit 10 is further provided with an orifice 13b for receiving stem portion 25b of cutting wire 25 and edge portion 13a extending about a segment of the circumference of cutting edge 12 for receiving the cutting blade 25a of cutting wire 25. Cutting blade 25a lies along the interior surface of conduit 10 along cut-away portion 12a. Plunger 15 is provided with a slot 15a for receiving pin 6 of drive means 5. Plunger 15 is mounted inside conduit 10 such that orifice 13b of conduit 10 is aligned with slot 16 of plunger 15 to receive stem portion 25b of cutting wire 25 simultaneously and in the same manner as orifice 13b of conduit 10 receives stem portion 25b.

Plunger 15 is further provided with a blunt end 15b for controlling the depth that conduit 10 enters the body of tissue and for maintaining the severed sample of tissue within a certain portion of conduit 10 until the solid severed tissue sample is expelled from apparatus 1. An outer sleeve 20 having a pronged tip 22 telescopically surrounds conduit 10 and sleeve portion 9 to support cutting wire 25 when it has been properly inserted into conduit 10 and plunger 15, respectively. Sleeve portion 9 of the FIG. 1 apparatus is further provided with an L-shaped travel slot 4 configured such that pin 6 is allowed to move about the complete distance of slot 4. Drive means 5 is further provided with a yoke 3 and a cam 5a, which advances conduit 10 in a forward direction when drive means 5 is activated in response to trigger 7 being depressed to close an electrical circuit to energize drive means 5. Apparatus 1 is further provided with a reset knob 2.

FIGS. 2 through 12 illustrate various fragmentary segments of the FIG. 1 apparatus in various alternative positions. These figures will be discussed in more detail in turn, as their individual descriptions become necessary to illustrate the operation of the FIG. 1 apparatus.

When in operation, conduit 10 and plungers 15 are each connected to the drive means 5 in the manner described above. Cutting wire 25 is inserted along slot 13 of conduit 10 with its stem portion 25b inserted in orifice 13b of conduit 10 and its blade portion 25a lying along conduit cutaway portion 12a. When trigger 7 is manually depressed it closes an electrical circuit housed within handle portion 1a of the FIG. 1 apparatus to connect a motor 11, also housed within handle portion 1a with a battery 30 to start drive means 5 to rotate. As drive means 5 rotates, a spring biased yoke 3 simultaneously causes cam 5a to be advanced in a forward direction as spring 3a is depressed by trigger 7. Cam 5a is connected to sleeve 9 to advance conduit 10 in a forward direction. As drive means 5 rotates, conduit 10 likewise rotates as conduit 10 is connected to drive means 5 by sleeve 9. Conduit 10 is also advanced in a forward direction since sleeve 9 is connected to cam 5a which is advanced by yoke 3. (See FIGS. 5 and 6).

Plunger 15 is also simultaneously rotated when drive means 5 is rotated to rotate conduit 10 and as cam 5a is advanced in a forward direction to likewise advance conduit 10 in a forward direction, as plunger 15 is connected to drive means 5 by pin 6. When drive means 5 is rotated, pin 6 (located on the surface of drive means (5) moves both axially and circumferentially along the entire distance of the L-shaped travel slot 4, as slot 4 is advanced in a forward direction by the movement of cam 5a and yoke 3, such that pin 6 of drive means 5 is in position 4a of slot 4. As conduit 10 is rotated and advanced, plunger 15 is likewise rotated but remains in a fixed position, axially, as mounted in conduit 10. The forward motion of conduit 10 into the body of tissue and of yoke 3 is limited by the forward movement of slot 4 to cause pin 6 to be located in position 4a of slot 4. At no time does outer sleeve 20, which is retained in its position by a retaining nut 26, move or rotate either axially or circumferentially relative to any other portion of apparatus 1. Pronged tip 22 of sleeve 20 does, however, hold the apparatus 1 in place against the body of tissue and prevent any torque movement of the apparatus as conduit 10 is rotated and advanced to penetrate the tissue surface.

Prior to trigger 7 being depressed and drive means 5 being energized, conduit 10, cutting wire 25 and plunger 15 are in the position illustrated in FIG. 2 with cutting blade 25a of cutting wire 25 lying in its rest position along the cutaway portion 12a of conduit 10. It is the rotational movement of plunger 15 and conduit 10 together with the forward movement of conduit 10 which occurs when drive means 5 is energized in response to trigger 7 being depressed, which causes cutting wire 25 to be rotated such that blade 25a of cutting wire 25 is moved in its cutting position, extending across the cutaway portion 12a of conduit 10. When conduit 10 is advanced by yoke 3 to penetrate the surface of the body of tissue, the cutting edge 12 of conduit 10 penetrates the surface of the tissue to detach the sample piece of tissue to be severed along its side walls from the remaining body of tissue. It is the subsequent movement of blade 25a across the remaining attached side of the sample of tissue which effects the complete severance of the sample piece of tissue from the body of tissue.

When trigger 7 is released, spring 3a removes the mechanical pressure from yoke 3 and the rotation of conduit 10, plunger 15 and drive means 5 stops due to the breakage of the electrical circuit which was previously closed when trigger 7 was depressed. Cutting wire 25 and conduit 10 remain in their FIG. 3 positions as pin 6 remains in position 4a of slot 4. Once a sampling of tissue 35 has been severed from the main body of tissue, a reset knob 2 is manually rotated by the operator to cause conduit 10 and wire 25 to return to their original positions as conduit 10 is connected to reset knob 2. Reset knob 2 is operatively connected to drive means 5 and plunger 15 such that when reset knob 2 is rotated drive means 5 and plunger 15 are likewise rotated in a direction opposite to the direction in which they were rotated when drive means 5 was initially energized by battery 30 and motor 11. Pin 6 is likewise returned to its original position by this manual operation of knob 2. Once conduit 10 is returned to its original position (FIG. 2) the tissue sample 35 is expelled from conduit 10. The disc of tissue 35 does, however, remain within conduit 10 until such time as reset knob 2 is manually operated. Pin 6 and plunger 15 remain in their stationary positions axially, relative to the return movement of conduit 10 as conduit 10 and wire 25 are withdrawn to the reset position (FIG. 2 and FIG. 4). Once cutting blade 25a is returned to its FIG. 2 and FIG. 4 positions sample 35 is expelled.

Figure 8:
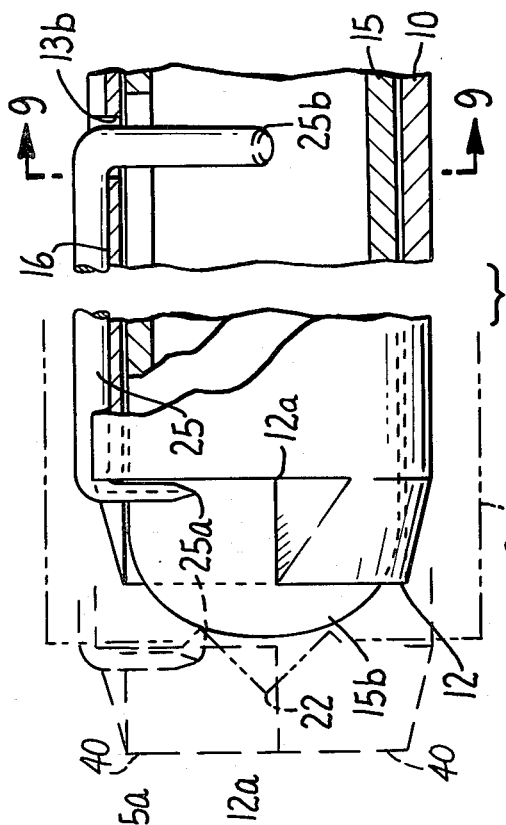
FIG. 8 is a fragmentary side view of the apparatus illustrating the movement of the cylindrical core as its cutting edge advances into the position of the dashed line to penetrate the body of tissue.
Figure 9:
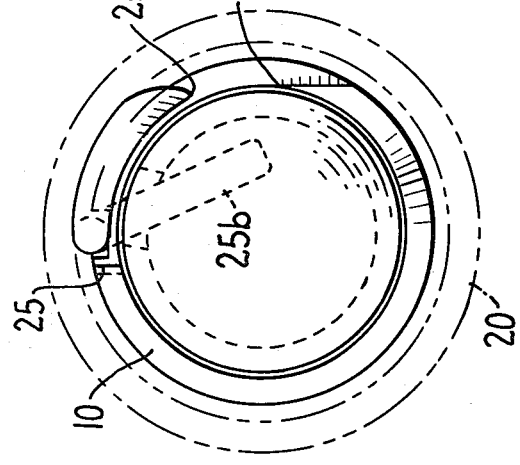
FIG. 9 illustrates the stem portion of the cutting blade taken along lines g—g of FIG. 8.

FIG. 8 illustrates the above described forward movement of conduit 10 as conduit 10 is rotated by drive means 5 and advanced in a forward direction by the operation of yoke 3a and cam 5a. As conduit 10 advances in the direction of the segmented line 40, conduit 10 penetrates the surface of the body of tissue from which a sampling of tissue is to be extracted. Simultaneously, as conduit 10 moves in the direction of segmented line 40, cutting blade 25a of wire 25 extends across the cutting edge 12 of conduit 10 including cutaway portion 12a to move in the cutting position to sever the sample of tissue from the main body of tissue. FIG. 7 illustrates an end view of the cutting blade 25a as it prepares to move in the cutting position as illustrated in FIG. 8. FIG. 9 likewise illustrates an enlarged end view of the stem portion 25b of cutting wire 25 as blade 25a prepares to move from the cutting position and as conduit 10 is being rotated and advanced in the position illustrated by segmented line 40.

Figure 10:
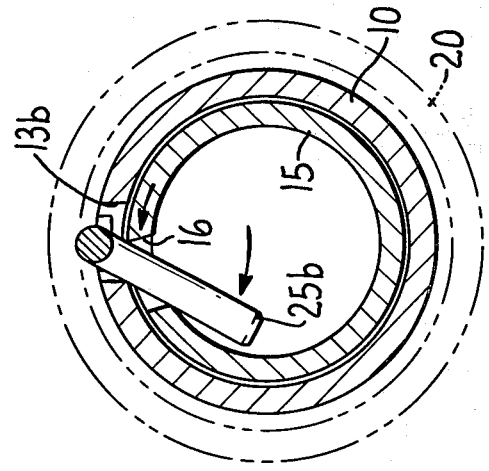
FIG. 10 is an enlarged end view of the cutting blade in the cutting position.
Figure 11:
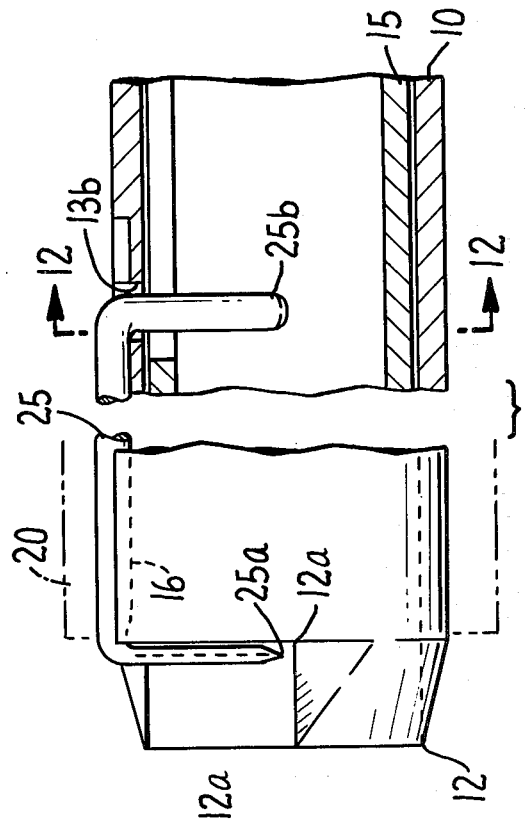
FIG. 11 is a fragmentary side view illustrating the cylindrical conduit of FIG. 8 with its cutting edge having penetrated the body of tissue and with the cutting blade in the cutting position.
Figure 12:
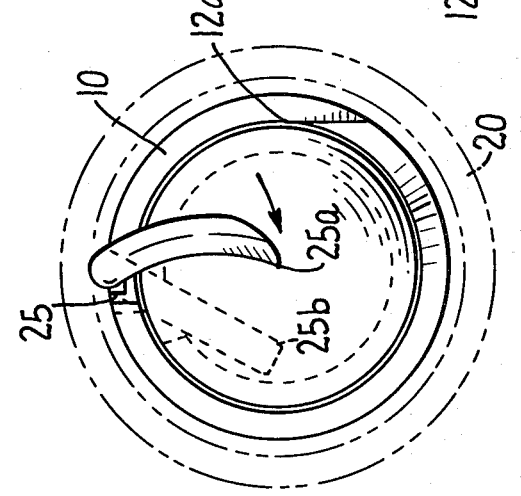
FIG. 12 illustrates the stem portion of the cutting blade taken along lines 12—12 of FIG. 11 when the cutting blade is in the cutting position.

FIG. 11 illustrates conduit 10 and cutting blade 25a of wire 25 in their cutting position to sever a sample of tissue from the main body of tissue. Conduit 10 has therefore been rotated by drive means 5 and advanced in a forward direction to penetrate the surface of tissue by yoke 3 and cam 5a. FIG. 10 is an enlarged end view illustrating cutting blade 25 in the cutting position to sever the sample of tissue from the main body. FIG. 12 likewise illustrates a large end view of wire stem 25b when cutting blade 25a is in the cutting position.

Certain further advantages of the invented apparatus need to be discussed at this point. For example, this apparatus is designed to operate on a minimum amount of power such as one (2) 2.4 volt C size battery. Also, it must be pointed out that the sample of tissue to be extracted from the main body of tissue may be of a predetermined size and shape, since the length of the sample to be extracted is determined by the length of the travel slot 4 through which pin 6 travels to its slot position of 4a on slot 4, and the diameter of the sample is determined by the inner diameter of conduit 10. Also, the extracted sample of tissue will have few, if any, distortions, thereby resulting in a far more accurate testing done on the sample. The device is also designed to be operated with ease and with minimal effort, and is further designed to be operated without the need for having to pretreat the body of tissue or the apparatus prior to extracting the sample. Despite the fact that the apparatus is capable of being operated from a very low power source, where a battery is used as a power source, it is possible to extract some twenty or more samples prior to having to recharge the power source.

While the disclosed apparatus has been illustrated in an embodiment it has been used to sever a sample of tissue from a body, namely the female cervix, it must be understood that the apparatus is useful in severing tissue from any suitable body be it plant or animal. The apparatus is likewise illustrated making use of a cutting wire for purposes of severing a tissue sample but it must be understood that any suitable cutting apparatus having a suitable blade portion may be used within the scope and spirit of the invented apparatus. The apparatus has also been illustrated to have an outer sleeve with prongs telescopically surrounding the cutting conduit and the plunger in order to support the stem portion of the cutting blade, to protect surrounding tissues from rotation with the prongs used to hold the apparatus in place during the cutting process, and to prevent slippage of the coring apparatus but it must be understood that the outer sleeve may be omitted and such a structure will still fall within the scope of the invention. The invention has thus been described in detail with particular reference to certain embodiments thereof, but it must be understood that variations and modifications can be effective within the spirit and the scope of the invention and the subject invention is unlimited by the scope of the intended claims.

What is claimed is:

1. Apparatus for extracting a sample of tissue from a body comprising:

a generally cylindrical conduit having a peripheral wall and a cutting end with the conduit having a circumferentially extending slot in the wall and an axially extending slot in the wall, a cutting edge formed on the cutting end of the conduit for cutting a core of tissue, a cutting blade having a blade portion faired within the circumferentially extending slot and a stem portion in the axially extending slot, means for pivoting the stem portion of said cutting blade to pivot the blade portion to a position projecting into the conduit to cut a disc of tissue from a core of tissue in the conduit; and a sleeve telescopically surrounding the conduit with the stem portion of the cutting blade being supported between the pivoting means and the sleeve.

2. The apparatus of claim 1 in which the means for pivoting comprises a plunger, having a slot in it, mounted inside the conduit movable axially of the conduit for ejecting the sample of tissue, and a lever integrally formed with the stem portion of the cutting blade and extending into the slot in the plunger.

3. The apparatus of claim 2 wherein the means for pivoting the stem include the following:

drive means, having an extended sleeve portion, for rotating the plunger;

means, including a pin about a portion of the surface of said drive means, for connecting said conduit and said plunger such that when said plunger is rotated, said conduit is simultaneously rotated and driven to cut the core; and an axially and then circumferentially extending slot on the surface of said extended sleeve portion of said drive means for receiving the pin to permit relative rotation of the conduit and plunger after the core is cut.

4. The apparatus according to claim 1 wherein said sleeve has a pronged tip about its edge adjacent the cutting edge of said conduit.

5. The apparatus of claim 1 wherein said cutting edge further comprises a cutaway portion such that when said blade portion of said cutting blade is pivoted to a position projecting into said conduit, said blade portion will extend across said cutaway portion to cut a sample of tissue from a core of tissue in the conduit.

6. A hand operated apparatus for automatically extracting a sample of tissue from a body comprising a generally cylindrical conduit having a cutting end and a remote end with the conduit having an axially facing cutting edge at the cutting end for cutting a core of tissue, a plunger mounted inside the conduit for movement with respect to the conduit both rotationally and axially, cutting means mounted in the conduit adjacent the cutting end for pivotal movement between a cutting position and a retracted position with the cutting means having a blade portion faired along the circumference of the conduit in the retracted position and pivotal inwardly toward the axis of the conduit to the cutting position responsive to relative rotation of the conduit and plunger, and drive means for rotating the conduit and plunger and reciprocating the plunger whereby (a) rotation of the conduit and plunger together with the cutting means in the retracted position permits the conduit to cut a core of tissue, (b) relative rotation of the core and plunger moves the cutting means to the cutting position, (c) rotation of the conduit and plunger together with the cutting means in the cutting position permits the cutting means to sever a sampling of tissue from a tissue core, and (d) axial motion of the plunger with respect to the conduit can expel a tissue sample.

* * * * *